Figure 1:
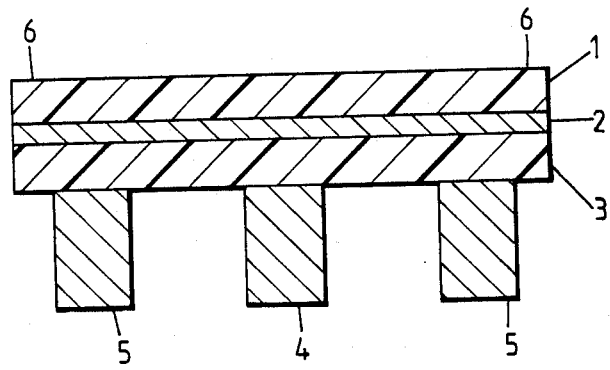

United States Patent [19]

Vadgama et al.

[11] Patent Number: 4,832,797
[45] Date of Patent: May 23, 1989

[54] ENZYME ELECTRODE AND MEMBRANE

[75] Inventors: Pankaj M. Vadgama; William H. Mullen, both of Newcastle-Upon-Tyne; Graham W. Scott, Northwich, all of England

[73] Assignee: Imperial Chemical Industries PLC, London, England

[21] Appl. No.: 936,720

[22] Filed: Nov. 25, 1986

[30] Foreign Application Priority Data

Nov. 28, 1985 [GB] United Kingdom ............... 8529300

[51] Int. Cl.[4] ...................... C25B 15/00; C25B 11/00
[52] U.S. Cl. ................................... 204/1 T; 204/403; 204/415; 210/500.27; 210/500.41
[58] Field of Search ................ 204/403, 415, 1 T; 210/500.27, 500.41

[56] References Cited

U.S. PATENT DOCUMENTS

| | | | |
|---|---|---|---|
| 3,539,455 | 11/1970 | Clark | 204/408 |
| 3,979,274 | 9/1976 | Newman | 204/403 |
| 4,026,977 | 5/1977 | Bourganel | 210/651 |
| 4,054,707 | 10/1977 | Quentin | 210/651 |
| 4,207,182 | 6/1980 | Marze | 210/500.41 |
| 4,356,074 | 10/1982 | Johnson | 204/403 |
| 4,361,484 | 11/1982 | Larsson et al. | 210/651 |
| 4,388,166 | 6/1983 | Suzuki et al. | 204/403 |
| 4,404,066 | 9/1983 | Johnson | 204/403 |

FOREIGN PATENT DOCUMENTS

| | | |
|---|---|---|
| 0008894 | 8/1979 | European Pat. Off. . |
| 0041780 | 12/1981 | European Pat. Off. . |
| 0145305 | 6/1985 | European Pat. Off. . |

OTHER PUBLICATIONS

Annals of the New York Academy of Science, 102, pp. 29–45, 1962.
Abstracts of Japanese Laid Open Patent Specifications (Kokais) 60185153 and 60185155.
Abstracts of European Pat. Nos. 1879, 8894, 8895, 41780 and 145305.

*Primary Examiner*—John F. Niebling
*Assistant Examiner*—Steven P. Marquis
*Attorney, Agent, or Firm*—Cushman, Darby & Cushman

[57] ABSTRACT

A membrane particularly for use in a sensor of the enzyme-electrode type which comprises one or more layers of material and an enzyme-containing layer and in which one layer is formed from a sulphonated or unsulphonated polyarylsulphone or a sulphonated or unsulphonated polyarylketone. The specification also relates to a non-enzymic sensor having a membrane including a layer formed from one of these polymers. Methods for determining an analyte using an enzymic or non-enzymic sensors are also included in the scope of the invention.

5 Claims, 1 Drawing Sheet

ENZYME ELECTRODE AND MEMBRANE

This invention relates to a membrane having improved properties for a sensor of the enzyme-electrode type, to a sensor which in particular is a sensor of the enzyme-electrode type comprising the improved membrane and to an analytical method which in particular is a method using an enzyme-electrode type sensor comprising an improved membrane.

Enzyme electrodes are increasingly used in medical and other laboratories particularly for the determination of materials such as glucose and urea in specimens of blood and other physiological fluids. Such electrodes are described in many publications notably an article by Clark and Lyons (Annals of the New York Academy of Science, 102, 29–45, 1962) and U.S. Pat. Nos. 3539455 and 3979274 to Clark and Newman respectively. Enzyme electrodes are generally used to determine materials which themselves are not electrochemically active but which in the presence of suitable enzymes take part in reactions which produce species which can be readily detected by the electrodes. In enzyme electrodes the enzymes are frequently located on polymeric membranes in close contact with the underlying electrode.

A considerable amount of research has been carried out in order to improve the properties of membranes for use in enzyme electrodes and many membranes for this purpose have been disclosed. An example of a type of membrane which is often used is the laminated membrane disclosed by Newman in U.S. Pat. No. 3979274. This membrane comprises an inner layer of an essentially homogeneous material, for example cellulose acetate, which can prevent the passage of materials of even low molecular weight likely to interfere with the enzyme-mediated signal, a closely opposed layer of the enzyme itself (with or without such other materials that may be blended with it), and an outer layer of a porous support film which can prevent the passage of cellular and colloidal elements.

The determination of glucose can be taken as an example of the determination of a material by an enzyme electrode. In the presence of the enzyme glucose oxidase the following reaction occurs:

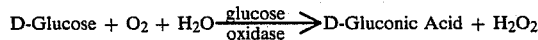

The hydrogen peroxide produced in this reaction passes through the inner layer of a membrane such as that of U.S. Pat. No. 3979274 and can be determined using the electrode. Since the hydrogen peroxide produced is dependent upon the glucose present in a specimen, the glucose concentration can be determined using a suitably calibrated sensor.

To date a number of difficulties have limited the utility of enzyme electrodes and restricted the scale of their use in routine analysis of, e.g. blood samples. An important difficulty is the effect of interfering species in the sample under test which can themselves give rise to a signal thereby enhancing the overall signal and causing an electrode to give a reading which is too high. For example when an enzyme-electrode is used to measure glucose in blood the enzyme-mediated signal produced may be appropriate but the observed signal may be elevated by a number of other species in the blood such as ascrobic acid which can give direct electrochemical signals at the hydrogen-peroxide detecting electrode.

According to the present invention we provide a membrane permeable to liquids and solutes which comprises an enzyme-containing layer and one or more layers of material wherein at least one layer of material is formed from a sulphonated or unsulphonated polyarylsulphone or a sulphonated or unsulphonated polyarylketone.

Further according to the present invention we provide a sensor which incorporates a membrane permeable to liquids and solutes and comprising one or more layers of material wherein at least one layer of material is formed from a sulphonated or unsulphonated polyarylsulphone or a sulphonated or unsulphonated polyarylketone.

Further according to the present invention we provide a sensor of the enzyme-electrode type which incorporates a membrane permeable to liquids and solutes and comprising an enzyme-containing layer and one or more layers of material wherein at least one layer of material is formed from a sulphonated or unsulphonated polyarylsulphone or a sulphonated or unsulphonated polyarylketone.

Further according to the invention we provide a method for determining an analyte in a specimen which comprises bringing the speciment into contact with the outer face of a membrane, permeable to liquids and solutes and comprising one or more layers of material, incorporated into a sensor sensitive to the analyte and measuring the response of the sensor to the analyte wherein at least one layer of material is formed from a sulphonated or unsulphonated polyarylsulphone or a sulphonated or unsulphonated polyarylketone.

Further according to the invention we provide a method for determining an analyte in a specimen which comprises bringing the speciment into contact with the outer face of a membrane, permeable to liquids and solutes and comprising an enzyme, in the presence of which the analyte is convertable into a species detectable by a sensor which incorporates the membrane, and one or more layers of material, and measuring the response of the sensor to the species, wherein at least one layer of material is formed from a sulphonated or unsulphonated polyarylsulphone or a sulphonated or unsulphonated polyarylketone.

Throughout the remainder of this specification the term sulphonated or unsulphonated polyarylsulphone will be abbreviated to PAS and the term sulphonated or unsulphonated polyarylketone will be abbreviaged to PAK.

The sensor of the invention is not restricted to sensors of the enzyme-electrode type and includes sensors incorporating membranes which do not comprise enzyme layers. The membranes in such non-enzyme type sensors comprise one or a plurality of layers of layers of material, the laminated membranes being formed from layers of the same or different materials.

When the sensor of the invention is a sensor of the enzyme-electrode type, the simplest form of the membrane in it and the simplest form of the membrane of the invention consists of the enzyme-containing layer and the layer formed from a PAS or a PAK with the latter layer preferably positioned between the enzyme-containing layer and the electrode.

It is preferred however that the membrane of the invention and the membrane in enzyme-electrode type sensors of the invention is a laminated membrane of the type of which that disclosed in U.S. Pat. No. 3979274 is an example. Such a membrane comprises a first or inner layer of material positioned between the enzyme-containing layer and the electrode, the enzyme-containing layer and a second layer of material on the other side of the enzyme-containing layer which second layer may be a layer having restricted permeability. It is much preferred that the first layer should be formed from a PAS or a PAK.

Generally the porous material of restricted permeability used in the second layer will be a polymeric material but other suitable materials may be used. Thus the second layer may be formed from a glass or a metal having pores cut by lasers.

Hereafter in this specification the enzyme-electrode type sensor of the invention which is described will contain a laminated membrane of the type of which the membrane described in U.S. Pat. No. 3979274 is an example having first and second polymer layers.

It should be understood that the membrane of the invention can contain more than two layers of material. For instance the second layer is not necessarily the outermost layer of the membrane. There may be a further layer or layers of material, i.e. third, fourth etc layers, between the second layer and a specimen. Often however the second layer will be the outer layer and its outer face will be contacted by the specimen in the method of the invention.

Any suitable PAS or PAK may be used in the membrane of the invention. However many of the polymers used will be materials which contain repeating units of the general formula A;

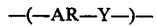  A wherein

Ar is a divalent aromatic radical and optionally, but preferably, at least some of the groups Ar are sulphonated; and Y is —SO$_2$— or —CO—.

The group Ar is preferably a group containing at least two aromatic rings which may be fused together or linked together by a direct bond, or linked together by an aliphatic group, an oxygen or sulphur atom or a sulphone or ketone group.

Preferably the PAS or PAK is a sulphonated polymer and in particular is a sulphonated polyarylethersulphone or a sulphonated polyaryletherketone in which the group Ar contains at least two aromatic groups linked together by an oxygen atom.

Sulphonated polymers of this type include polymers which contain repeating units of the formula B;

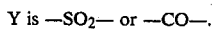  B wherein

Y is as defined;

Ph$^1$ represents a phenylene residue, preferably a paraphenylene residue, wherein at least some of the groups Ph$^1$ are sulphonated; and n is 1 or 2 and the value of n can differ along the polymer chain.

If the group Y is a —SO$_2$— group in the sulphonated polymer of formula B, the value of n may be only one or only two, but we prefer to use a copolymer in which the value of n is one for some repeating units and is two for other repeating units. Such copolymers, and the preparation thereof, are disclosed in European Patent Specification No. 8894. Suitable sulphonated polysulphones have repeating units of the formula C:

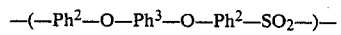  C together with the repeating units of the formula D:

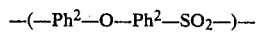  D wherein

Ph$^2$ represents a phenylene residue, preferably a paraphenylene residue;

Ph$^3$ represents a phenylene residue, preferably a paraphenylene residue, having one or two groups —SO$_3$M;

M is a hydrogen atom, a metal atom and/or a group NR$_4$, wherein the groups M may be the same or different and the proportion of the groups M is sufficient to combine with the unsatisfied valencies of the group —SO$_3$; and R is a hydrogen atom or an alkyl group.

The sulphonated polysulphone may also include a proportion of unsulphonated copolymer having repeating units of the formula E:

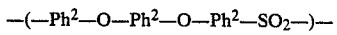  E together with the repeating units of the formula D and the formula E, wherein Ph$^2$ is as defined.

In the repeating units of the formula C, when Ph$^3$ is an ortho- or para-phenylene residue, there is typically only one group —SO$_3$M whereas, when Ph$^3$ is a meta-phenylene residue, there are typically two groups —SO$_3$M. When Ph$^3$ is an ortho-phenylene residue, the —SO$_3$M group is located in a position which is para- to one ether group and meta- to the other ether group, any further sulphonation occurring to locate the —SO$_4$M in positions meta- to each other. When Ph$^3$ is a para-phenylene residue, the —SO$_3$M group is located in a position ortho- to one ether group and meta- to the other ether group. When Ph$^3$ is a meta-phenylene residue, the —SO$_3$M groups are located in the position ortho- to one ether group and para- to the other ether group.

The sulphonated copolymers may be prepared by sulphonating a copolymer consisting of repeating units D and E. The sulphonation is readily effected by dissolving the copolymer in concentrated sulphuric acid (98% w/w) at ambient temperature and agitating the mixture for a sufficient time for sulphonation of essentially all of the sub-units —O—Ph$^2$—O— in the repeat units of formula E. The copolymers which are subjected to sulphonation suitably have from 1 to 99 mole % of units E and correspondingly from 99 to 1 mole % of units D, and especially from 5 to 80 mole % of units E and correspondingly from 95 to 20 mole % of units D. Sulphonation is desirably effected to convert at least 90% of the units E to the units C.

The sulphonated polysulphones are polymeric materials of high molecular weight such that the reduced viscosity (RV) of the polymer, (measured as a 1% by weight solution of the polymer in dimethylformamide at 25° C.) is at least 0.2 and preferably at least 0.4. The polymer may be such as to give an RV of up to 2.5, but it is generally preferred that the RV of the polymer does not exceed 2.0.

The sulphonated polysulphone contains the groups —SO$_3$M, where M may be hydrogen, a metal atom or a group NR4. Sulphonated polysulphones in which M is a divalent metal atom, particularly an alkaline earth metal, are the subject of our published European Patent Application No. 145305, which also discloses a method for the production of such divalent metals salts and the use thereof for the production of asymmetric semipermeable membranes.

Less preferably the membrane can contain a layer formed from a material of formula B in which the group Y is a ketone group. Sulphonated polyketones which may be used include polymers which contain repeating units of the formula F:

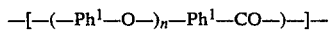   F wherein $Ph^1$ and n are as defined.

The sulphonated polyketone may be a material in which the value of n is only one or is only two or in which the value of n differs along the polymer chain and is both one and two at various points along the chain. Thus, the sulphonated polyketone may be a material obtained by sulphonating a polyketone having only the repeating units G:

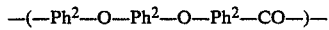   G or only the repeating units H:

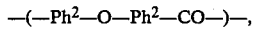,   H wherein $Ph^2$ is as defined.

Alternatively, the sulphonated polyketone may be obtained by sulphonating a copolymer having both the repeating units G and the repeating units H. In the polyketone which is to be sulphonated, it is preferred that the groups $Ph^2$ are paraphenylene groups.

Sulphonated polyketones which may be used are described in the prior art, for example in European Patent Specifications Nos. 8895 and 41780. Thus, it is possible to use the products obtained by sulphonating a polymer having the repeating units of the formula G, optionally together with other repeat units. Sulphonation may be effected by dissolving the polyketone in concentrated sulphuric acid (98% w/w) and agitating the solution until the polymer has been sulphonated to a desired extent. The sulphonation in concentrated sulphuric acid may be carried out at ambient temperature or at an elevated temperature, for example at least 50° C., depending on the polyketone to be sulphonated.

The polyketone which is sulphonated is preferably one containing the repeating units of the formula G only or a copolymer containing the repeating units of the formula G together with up to 50 mole % of comonomer units of the formula J:

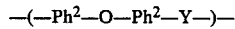   J or comonomer units of the formula E (as herein described) where $Ph^2$ and Y are both as defined.

Preferred sulphonated polyketones contain the repeating units K:

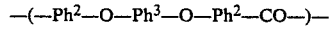   K together with the repeating units G and optionally also the repeating units H, wherein
$Ph^2$ and $Ph^3$ are both as defined.

The sulphonated polyketones are conveniently prepared by sulphonation of polyetherketones using the procedures described herein and in European Patent Specifications Nos. 8895 and 41780. The polyetherketones which are sulphonated suitably crystalline polymers containing the repeating units G alone or together with other repeating units and having an RV (measured at 25° C. in a 0.1% w/w solution of the polymer in concentrated sulphuric acid) of at least 0.7. Such polymers are more fully described in European Patent Specification No. 1879.

The sulphonated polyarylsulphones are preferred to the sulphonated polyarylketones. The polymers are conveniently those having a sulphonation ratio of at least 2, for example at least 4, and not more than 20, preferably not more than 15. By "sulphonation ratio" is meant the ratio of the number of unsulphonated phenylene residues in the sulphonated polymer to the number of sulphonated phenylene residues in the sulphonated polymer. The sulphonation ratio can be determined by titration or by n.m.r. In the sulphonated polysulphone, the group —$SO_3M$ may be in the free acid form as —$SO_3H$ or may be a salt, for example an ammonium salt or a salt of a metal such as sodium, calcium, barium or a metal of Group VIII of the Periodic Table.

In the membrane of the invention it is preferred that the first layer of material, i.e. that between the enzyme and the electrode is formed from the PAS or PAK. Suitably the first layer has a thickness in the range 0.2 to 1.0 microns.

The second polymeric layer in the membrane of the invention acts as a permeability barrier and prevents or restricts the passage of compounds of high molecular weight and gives strength to the membrane sufficient to enable it to retain its shape and to maintain suitable contact with the electrode. Suitable polymeric materials for the second layer include porous polycarbonates, polyurethanes and modified cellulose, such as cellulose acetate. Suitable materials also include materials having a percentage porosity (the product of pore area X pore density X100) which is not greater than 5% and preferably in the range 0.001% to 0.5%. Often such materials will have pores of mean diameter less than 0.03 microns. To ensure rapid electrode response the thickness of the second polymeric layer is preferably less than 20 microns, especially in the range 1 to 10 microns. Especially suitable polymeric materials for the second layer are the materials having a percentage porosity not greater than 5% which are used for a similar purpose in the sensors of our copending European Patent Application No. 86307011.6 In such materials the permeability of the second layer is restricted to an extent such that the rate of permeation of the analyte across the layer is the rate limiting step for its reaction with the sensor.

The enzyme present in the membrane of the invention may be located therein in any suitable manner. Preferably in a laminated membrane it is present between the first and second layers of material and causes them to adhere together. In this situation and also generally, the enzyme is preferably immobilised by mixing with a material which causes cross linking to occur. A very suitable material for this purpose is glutaraldehyde; proteins such as albumin and other materials may also be included. In order to facilitate the obtaining of rapid stable readings from the sensor incorporating the membrane it is preferred that the enzyme-containing layer is thin, i.e. not greater than 50 microns thick.

The enzyme to be used in the membrane of the invention will depend upon the analyte whose concentration is to be determined. If the analyte is glucose then the enzyme will be for example glucose oxidase. Other enzymes which may be present include uricase and lactate oxidase for determination of uric acid and lactic acid respectively.

The outer face of the outermost layer of the membrane, i.e. that face which contacts the specimen, may if desired be treated with an organo-silane as described in our European Patent Application No. 86303907.9.

A laminated membrane for use in the sensor of the invention for the determination of glucose may be prepared by a method including the following steps:

1. 1 mg glucose oxidase is dissolved in 50 μl of (100 mg/ml) albumin:
2. 3 μl of 12.5% glutaraldehyde solution is mixed with 3 μl of the enzyme/albumin mixture on a glass microscope slide:
3. 1 μl of the mixture produced in the previous step is applied to one face of a 1 cm² polycarbonate film having pores with a mean diameter below 0.03 microns:
4. The other surface of the enzyme layer is covered immediately with a thin sulphonated polysulphone film and the resulting laminated membrane is clamped for 3 minutes between glass slides. After removal from the glass slides the laminated membrane produced by the above sequence of steps may be applied to a platinum electrode to form the sensor of the invention, the sulphonated polysulphone film being nearest to the electrode and forming the first layer.

In addition to the method described above in which the first or inner layer of PAS is formed by pressing out a droplet of polymer solution between 2 glass slides other methods are possible. For instance a spin coater could be used with optimisation of droplet size, polymer concentration, spin speed and time. Any type of spin coater could be used including the flat chuck type. Such a method should be capable of producing films of 1 μm or less reproducibly. Other methods include a variety of printing techniques such as screen or gravure and use of a water or other liquid surface on which to cast the film. Casting onto water gives the possibility of obtaining extremely thin films and controlling orientation and surface compaction. These methods allow a film to be cast directly onto an electrode assembly or, in the case of the liquid surface the film can be picked up onto the electrode avoiding unnecessary handling.

The sensor of the invention may have a detachable membrane or it may be a disposable sensor with an adherent membrane. Materials used in the formation of suitable electrodes for the sensors include inert metals and/or carbon. The electrode assembly may be formed by vacuum evaporation sputtering or ion-plating on to a substrate.

Use of the analytical method of the invention has the advantage that it enables the effect of interfering species on the signal to be measured by the sensor to be greatly reduced or in some cases effectively eliminated. This greatly increase the reliability of the enzyme-electrode sensors of the invention.

Figure 2:
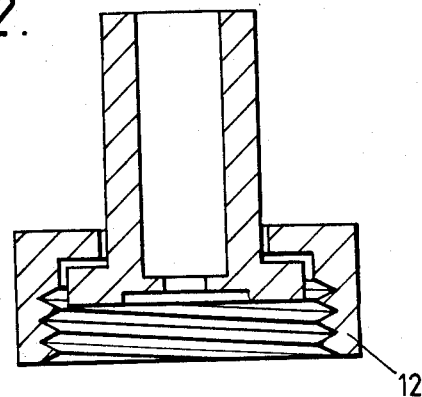
Figure 2:
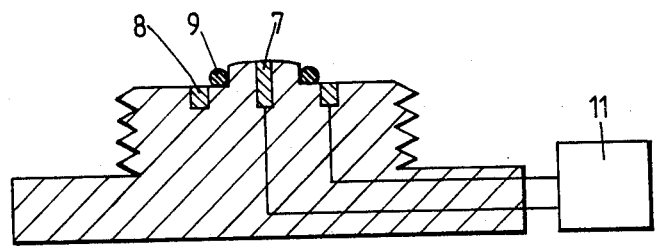

The invention is illustrated by FIGS. 1 and 2 of the accompanying drawings wherein:

FIG. 1 shows in cross-section part of an enzyme-electrode type sensor with a membrane of the invention attached thereto; and FIG. 2 is an exploded cross-sectional view of part of a sensor of the invention for the determination of hydrogen peroxide.

In FIG. 1, reference numeral 1 is the second polymer layer of the membrane formed from a polycarbonate film having pores of mean diameter below 0.03 microns and having a percentage porosity which is not greater than 5%, 2 is a layer of glucose oxidase enzyme dissolved in albumin and mixed with glutaraldehyde, 3 is the first polymer layer formed from a sulphonated polysulphone, 4 is the platinum working electrode and 5 is the silver reference electrode. 1, 2 and 3 together form a laminated membrane. Platinum working electrode 4 acts as an anode whilst silver reference electrode 5 acts as a cathode. The membrane is held in place on the electrode by a perspex ring pressing down on outer layer 1 towards its outer edges at 6.

In FIG. 2, reference numeral 7 is a platinum working electrode polarised at +6.50 mV against the reference electrode, 8 is a silver/silver chloride reference electrode, 9 is a sealing 'O' ring, 10 is a sulphonated polysulphone membrane, 11 is a current meter and source of polarising voltage and 12 is a screwfit top with sample compartment. To place this sensor in a condition for use, a few drops of a buffer solution containing 50 m mol $l^{-1}$ sodium chloride is applied to the surface of the sensor to provide electrolytic contact between the working and reference electrodes 7 and 8 respectively. The sulphonated polysulphone membrane 10 is then placed over the working electrode 7 and held in place by screw-fit top 12 of the electrode body. The sensor is now ready to measure aqueous solutions of hydrogen peroxide.

Membrane formation

The sulphonated polysulphone films for the membranes of the enzyme-electrode type sensor of FIG. 1 and the sensor of FIG. 2 were cast from a 10% w/v solution of sulphonated polysulphone (5, 10 or 20 sulphonation ratios tried; 10 type exemplified herein) in dimethyl sulphoxide. 50 μl of solution was spread evenly over a glass plate of surface area 20 cm². The plate was placed in a vacuum oven and left at 0.1 mm Hg, 50° C. for 6 hrs.

NB: The polymers had the following RV: 5−RV=0.95: 10−RV=0.86 and 20−RV=0.70.

The use of the enzyme-electrode type sensor shown in FIG. 1 is illustrated in the following Example:

EXAMPLE

One of the main problems in the use of glucose enzyme electrodes for blood measurements is the effect of interfering species in blood such as ascorbic acid, which give a direct electrochemical signal at an $H_2O_2$-detecting electrode. This example illustrates how the sulphonated polysulphone layer in the membrane of the invention may be used to screen out these interfering species and allow selective measurement of $H_2O_2$, formed from the reaction of the enzyme glucose oxidase (EC 1.1.3.4) with its substrates, glucose and oxygen.

A solution (10 μl) containing 3 mg ml$^{-1}$ glucose oxidase and 200 mg ml$^{-1}$ serum albumin was mixed with a 5% aqueous solution of glutaraldehyde (5 μl), and left to become viscous. 2 μl of the mixture was applied to one side of a polycarbonate film (1 cm²) having pores of mean diameter 0.015 μm. Onto the enzyme layer was pressed a 1 cm² piece of sulphonated polysulphone film and the laminate was left to allow the enzyme to crosslink further. The laminate can then be used as a substitute for the plain sulphonated polysulphone membrane in the sensor of FIG. 2 or can be used in the sensor of FIG. 1 to provide an enzyme electrode responsive to glucose solutions. In the sensor the laminate was positioned with the first sulphonated polysulphone layer facing towards the sensor surface.

The Table gives the results obtained when the laminate membrane was used in the presence of glucose and glucose with various interfering species. In the Table the results are compared with the results obtained with a membrane lacking the sulphonated polysulphone layer. It can be seen that the membrane with the sulphonated polysulphone layer gave a response which was much less affected by interfering species than that of the conventional membrane.

TABLE

| Solutes | Response | | | |
|---|---|---|---|---|
| | Conventional enzymic membrane (arbitrary units) | % increase | Enzymic membrane with sulphonated polysulphone first layer | % increase |
| (a) 1 mmol 1$^{-1}$ glucose - alone | 9 | | 4.2 | |
| (b) +0.2 mmol 1$^{-1}$ ascorbic acid | 14.5 | 60 | 4.3 | 2 |
| (c) +0.1 mmol 1$^{-1}$ cysteine | 9.9 | 10 | 4.2 | 0 |
| (d) +1 mmol 1$^{-1}$ glutathione | 11.5 | 28 | 4.2 | 0 |
| (e) +0.5 mmol 1$^{-1}$ urate | 26 | 190 | 4.2 | 0 |
| (f) a solution containing all the above ingredients | 33 | 270 | 4.4 | 5 |
| (g) 1 mmol 1$^{-1}$ glucose + 1 mmol 1$^{-1}$ acetaminophen | 78 | 770 | 5.0 | 20 |

We claim:

1. An enzyme electrode sensor which comprises an electrode and a membrane permeable to liquids and solutes said membrane comprising an enzyme-containing layer and at least one layer of material positioned between the enzyme containing layer and the electrode wherein said at least one layer of material is formed from a homogeneous polymer selected from the group consisting of a sulphonated and an unsulphonated polyarylsulphone and a sulphonated and an unsulphonated polyarylketone.

2. A sensor according to claim 1 in which the membrane comprises a first layer of material positioned between the enzyme-containing layer and the electrode, the enzyme-containing layer and a second layer of material on the other side of the enzyme-containing layer wherein the first layer is formed from a polymer selected from the group consisting of a sulphonated and an unsulphonated polyarylsulphone and a sulphonated and an unsulphonated polyarylketone.

3. A sensor according to claim 1 wherein the first layer has a thickness in the range of 0.2 to 1.0 microns.

4. A sensor according to claim 1 wherein the second layer is formed from a polymeric material having a percentage porosity in the range 0.001% to 0.5%.

5. A method for determining an analyte in a specimen which comprises bringing the specimen into contact with the outer face of a membrane, permeable to liquids and solutes and comprising an enzyme, in the presence of which the analyte is convertable into a species detectable by a sensor which comprises an electrode and the membrane, and one or more layers of material, and measuring the response of the sensor to the species, wherein at least one layer of material is formed from a homogeneous polymer selected from the group consisting of a sulphonated and an unsulphonated polyarylsulphone and a sulphonated and an unsulphonated polyarylketone.

* * * * *